United States Patent [19]

Schirmer et al.

[11] 4,283,547

[45] Aug. 11, 1981

[54] PARABANIC ACID DERIVATIVES

[75] Inventors: Ulrich Schirmer, Heidelberg; Rainer Becker, Bad Durkheim; Bruno Wuerzer, Otterstadt, all of Fed. Rep. of Germany

[73] Assignee: BASF Aktiengesellschaft, Fed. Rep. of Germany

[21] Appl. No.: 132,983

[22] Filed: Mar. 24, 1980

[30] Foreign Application Priority Data

Apr. 25, 1979 [DE] Fed. Rep. of Germany ....... 2916647

[51] Int. Cl.³ .......................................... C07D 233/96
[52] U.S. Cl. ........................................ 548/307; 71/92
[58] Field of Search ........................................ 548/307

[56] References Cited

U.S. PATENT DOCUMENTS

| | | | |
|---|---|---|---|
| 2,463,986 | 3/1949 | Longley | 548/307 |
| 2,895,817 | 7/1959 | Luckenbaugh | 548/307 |
| 3,418,334 | 12/1968 | Stoffel | 548/307 |
| 3,822,282 | 7/1974 | Singer | 548/307 |
| 3,956,308 | 5/1976 | Cleveland | 548/307 |

*Primary Examiner*—Henry R. Jiles
*Assistant Examiner*—Natalia Harkaway
*Attorney, Agent, or Firm*—Keil & Witherspoon

[57] ABSTRACT

New and valuable parabanic acid derivatives having a herbicidal action, herbicides containing these compounds, processes for controlling the growth of unwanted plants with these compounds, and processes for manufacturing these herbicides.

3 Claims, No Drawings

PARABANIC ACID DERIVATIVES

The present invention relates to new and valuable parabanic acid derivatives having a herbicidal action, herbicides containing these compounds, processes for controlling the growth of unwanted plants with these compounds, and processes for manufacturing these herbicides.

Unsubstituted and halogen-substituted 3-phenylparabanic acids have been disclosed as herbicides (U.S. Pat. No. 2,895,817). This publication describes their use for the complete elimination of unwanted vegetation. Special attention is drawn to the control of crabgrass (Digitaria spp.) in lawns by 1-methyl-3-phenylparabanic acid and 1-methyl-3-(p-chlorophenyl)-parabanic acid. The possibility of controlling seed weeds in Indian corn is also demonstrated.

We have now found that new parabanic acid derivatives of the formula

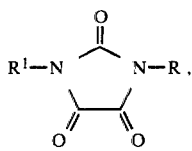

where $R^1$ denotes alkyl (e.g., methyl, isopropyl), alkoxyalkyl (e.g., methoxymethyl, methoxyethyl), haloalkyl (e.g., 2-chloroethyl), unsubstituted or alkyl-substituted cycloalkyl (e.g., cyclopropyl, cyclohexyl), unsubstituted or halogen- or alkoxy-substituted alkenyl (e.g., allyl), or unsubstituted or halogen- or alkoxy-substituted alkynyl (e.g., propargyl, butyn-(1)-yl-(3), 1-chlorobutyn-2-yl-(4)) and R denotes unsubstituted or fluoro-substituted o-fluorophenyl, or phenoxyphenyl which is unsubstituted or mono- or polysubstituted by alkyl, haloalkyl, alkoxyalkyl, cycloalkyl, aralkyl, halogen, alkoxy, haloalkoxy, alkylthio, nitro, aryl, thiocyanato, cyano,

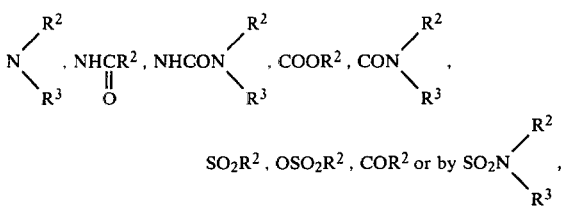

$R^2$ and $R^3$ being identical or different and each denoting hydrogen or having the meanings given for $R^1$, have on the one hand such a broad and strong herbicidal action that they may be used for the total control of unwanted plants or in perennial crops, and on the other are surprisingly tolerated by various annual crops.

$R^1$ in the formula may have for instance the following meanings: unsubstituted alkyl (1 to 4 carbon atoms), haloalkyl or alkoxyalkyl (e.g., methyl, ethyl, 2-chloroethyl, 2-methoxyethyl, methoxymethyl, isopropyl, n-propyl, n-butyl, sec-butyl, tert-butyl, isobutyl), unsubstituted or halogen-substituted alkenyl (e.g., allyl, 2-chloropropen-(1)-yl-(3), buten-(1)-yl-(3)), unsubstituted or halogen- or alkoxy-substituted alkynyl (e.g., propargyl, butyn-(1)-yl-(3), 1-chlorobutyn-(2)-yl-(4)), or unsubstituted or alkyl-substituted cycloalkyl (e.g., cyclopentyl, cyclohexyl, 3-methylcyclohexyl, 2,6-dimethylcyclohexyl, cyclopropyl).

The phenoxyphenyl radical may for example be substituted by alkyl (1 to 3 atoms) (e.g., methyl, isopropyl), haloalkyl (e.g., trifluoromethyl), alkoxyalkyl (e.g., methoxymethyl), cycloalkyl (e.g., cyclohexyl), aralkyl (e.g., benzyl), halogen (e.g., fluorine, chlorine, bromine and iodine), alkoxy (e.g., methoxy), haloalkoxy (e.g., trifluoromethoxy), alkylthio (e.g., methylthio), nitro, aryl (e.g., phenyl), thiocyanato, cyano,

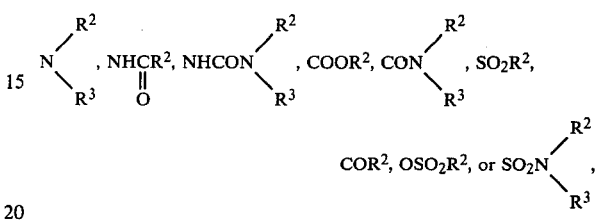

$R^2$ and $R^3$ being identical or different and each denoting hydrogen or having the meanings given for $R^1$.

The new compounds may be prepared for instance by the following processes—$R^1$ and R have the meanings given above.

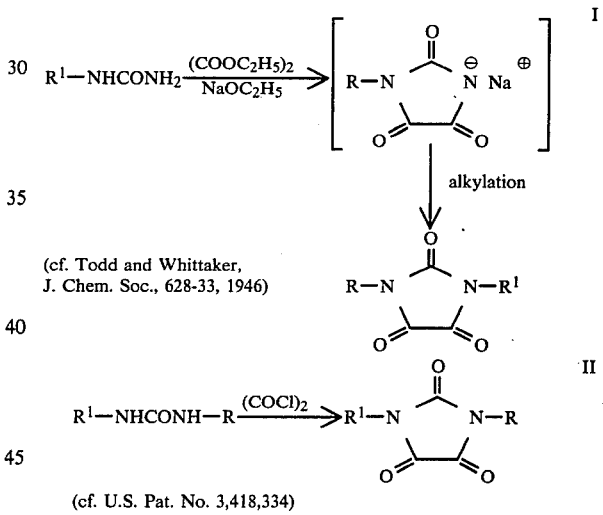

(cf. Todd and Whittaker, J. Chem. Soc., 628-33, 1946)

(cf. U.S. Pat. No. 3,418,334)

The preferred method of synthesis is described in more detail below.

1-Aryl-3-aliphatic ureas (obtainable by reaction of aliphatic isocyanates with aromatic amines, or by reaction of aryl isocyanates with aliphatic amines (e.g., German Laid-Open Applications DE-OS Nos. 2,048,660 and 2,558,078)) are reacted in a solvent inert under the reaction conditions, e.g., hydrocarbons (ligroin, gasoline, toluene, cyclohexane), halohydrocarbons (methylene chloride, chloroform, chlorobenzene, bromobenzene) or nitrohydrocarbons (e.g., nitrobenzene), with equimolar or excess amounts of oxalyl chloride at from 30° to 180° C. until no more hydrogen chloride evolves.

The following examples illustrate the preparation of the novel parabanic acid derivatives.

EXAMPLE 1

264 g of oxalyl chloride is dripped into 311 g of 1-(2'-fluorophenyl)-3-methylurea in 3 liters of chloroform, whereupon the reaction solution boils. The solution is refluxed for a further 8 hours and then concentrated. Petroleum ether is then added. The crystalline mash which precipitates out is filtered and dried. There is obtained 373 g of 1-(2'-fluorophenyl)-3-methylparabanic acid, m.p.: 140°–142° C. (No. 1).

The following parabanic acid derivatives may be prepared analogously:

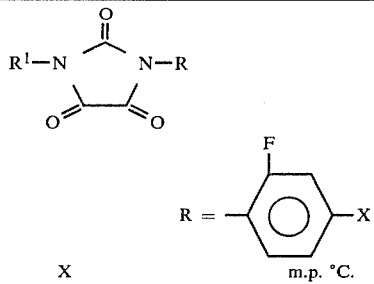

| No. | R¹ | X | m.p. °C. |
|---|---|---|---|
| 2 | ethyl | F | |
| 3 | methoxyethyl | H | |
| 4 | cyclopropyl | H | 133–135 |
| 5 | methoxymethyl | F | |
| 6 | 2-chloroethyl | H | |
| 7 | cyclohexyl | F | |
| 8 | allyl | F | |
| 9 | n-butyl | H | 85–87 |
| 10 | propargyl | H | |
| 11 | butyn-(1)-yl-(3) | F | |
| 12 | methoxymethyl | H | |
| 13 | methyl | F | 130–132 |
| 14 | 1-chlorobutyn-(2)-yl-(4) | H | |
| 15 | propargyl | F | |
| 16 | ethyl | H | |
| 17 | isopropyl | H | 111–113 |
| 18 | allyl | H | |
| 19 | isopropyl | F | |
| 20 | sec . butyl | H | |

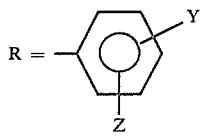

| No. | R¹ | Z | Y | m.p. °C. |
|---|---|---|---|---|
| 21 | methyl | 3-F | 4-phenoxy | 187–188 |
| 22 | ethyl | 3-OCH₃ | 4(3'bromophenoxy) | |
| 23 | methoxyethyl | 3-Cl | 4(3'methylphenoxy) | |
| 24 | methyl | 2-F | 4(4'fluorophenoxy) | |
| 25 | methyl | H | 4(3'fluorophenoxy) | 139 |
| 26 | methyl | 3-Cl | 4(4'methylphenoxy) | 179–182 |
| 27 | methyl | 3-F | 4(3'trifluoromethylphenoxy) | |
| 28 | ethyl | H | 4(4'cyclohexylphenoxy) | |
| 29 | 2-chloroethyl | 3-Cl | 4(3'nitrophenoxy) | |
| 30 | cyclohexyl | 3-Br | 4(4'methylthiophenoxy) | |
| 31 | methyl | 2-F | 4(3'methoxyphenoxy) | |
| 32 | methyl | 4-Cl | 3(4'chlorophenoxy) | |
| 33 | allyl | 4-Cl | 3(4'thiocyanatophenoxy) | |
| 34 | methyl | 4-Cl | 3-phenoxy | |
| 35 | propargyl | 3-OCHF₂ | 4-phenoxy | |
| 36 | methyl | H | 4-phenoxy | 185–188 |
| 37 | butyn(1)yl(3) | 3-Cl | 4(4'fluorophenoxy) | |
| 38 | methyl | 3-CF₃ | 4-phenoxy | |
| 39 | β-chlorobutyn(2)yl(4) | H | 4(3'cyanophenoxy) | |
| 40 | methyl | H | 4(3'methoxyphenoxy) | 105–107 |
| 41 | ethyl | 3-CH₃ | 4(3'acetylphenoxy) | |
| 42 | methyl | 2-F | 5-phenoxy | |
| 43 | isopropyl | 3-Br | 4(4'dimethylaminosulfonylphenoxy) | |
| 44 | methyl | 3-Cl | 4(3'methoxyphenoxy) | 150–151 |
| 45 | sec . butyl | 3-I | 4(3'methoxycarbonylphenoxy) | |
| 46 | methyl | 3-F | 4(4'fluorophenoxy) | |
| 47 | methyl | H | 4(4'methoxyphenoxy) | 180–181 |
| 48 | t-butyl | 3-OCH₃ | 4(4'dimethylaminocarbonylphenoxy) | |
| 49 | methyl | 3-SCH₃ | 4-phenoxy | |
| 50 | methyl | 3-CN | 4-phenoxy | |
| 51 | methyl | 3-F | 4(4'methoxyphenoxy) | 195–201 |
| 52 | ethyl | 3-NO₂ | 4(3'chlorophenoxy) | |
| 53 | cyclopropyl | 3-Cl | 4(3',4'dichlorophenoxy) | |
| 54 | methyl | 5-Cl,2-F | 4-phenoxy | |
| 55 | methyl | 3-Cl | 4-phenoxy | 157–158 |
| 56 | methyl | H | 4(2',4'dichlorophenoxy) | |

-continued

| | | | | |
|---|---|---|---|---|
| 57 | methoxymethyl | H | 3(4'chlorophenoxy) | |
| 58 | methyl | 3-Cl | 4(2',4'dichlorophenoxy) | |
| 59 | methyl | 5-F, 2-F | 4-phenoxy | |
| 60 | methyl | H | 4(3',5'dichlorophenoxy) | |
| 61 | ethyl | 3-F | 4(2'bromo-4'chlorophenoxy) | |
| 62 | methyl | 3-Cl | 4(4'methoxyphenoxy) | 150–152 |
| 63 | methyl | H | 4(2',4',5'trichlorophenoxy) | |
| 64 | methyl | 3-Cl | 4(4'chlorophenoxy) | 184–187 |
| 65 | methyl | 3-Cl | 4(4'difluoromethoxyphenoxy) | |
| 66 | methyl | H | 4(4'bromophenoxy) | |
| 67 | methyl | H | 4(4'difluoromethoxyphenoxy) | 176–178 |
| 68 | methyl | H | 4(4'chlorotrifluoroethoxyphenoxy) | 160–161 |

The influence of the compounds according to the invention on the growth of unwanted and crop plants is demonstrated in the following greenhouse experiments.

The vessels employed were plastic flowerpots having a volume of 300 cm³, and which were filled with a sandy loam containing about 1.5% humus. The seeds of the test plants (cf. Table 1) were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For postemergence treatment, the plants were first grown to a height of 3 to 10 cm, depending on the growth shape, before being treated. The vessels were not covered after treatment. The pots were set up in the greenhouse-species from warmer areas at from 25° to 40° C., and species from moderate climates at 15° to 30° C. The experiments were run for from 3 to 6 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The tables below show the herbicidal action of the new compounds and reveal for example their surprising tolerance by agricultural crops. The agents may be applied either pre- or postemergence, e.g., before the unwanted plants have germinated from seed or sprouted from vegetative plant parts, or to the leaves of the unwanted and crop plants. A further application technique may be used in which the agents are sprayed from suitable equipment in such a manner that the leaves of sensitive crop plants are if possible not touched, and the agents reach the soil or the unwanted plants growing beneath the crop plants (post-directed, lay-by treatment). Depending on the time of the year and the growth stage, application rates are from 0.1 to 15 kg/ha and more; the higher dosage rates are particularly suitable for the total elimination of vegetation.

In view of the many application methods possible, the agents according to the invention, or mixtures containing them, may be used not only on the crop plants listed in the tables, but also in a much larger range of crops for removing unwanted plants.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapas* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca saiva* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vularis* | snapbeans, green beans, dry beans |
| *Pennisetum glaucum* | |

| Botanical name | Common name |
| --- | --- |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

The parabanic acid derivatives may be mixed with each other, or mixed and applied together with numerous representatives of other herbicidal or growth-regulating active ingredient groups. Examples of suitable mixture components are diazines, N-phenylcarbamates, thiolcarbamates, diurethanes, halocarboxylic acids, phenoxy fatty acids, triazines, amides, ureas, diphenyl ethers, triazones, uracils, benzofuran derivatives, etc. Such combinations extend the spectrum of action, and synergistic effects are sometimes achieved. A number of active ingredients which give, with the new compounds, mixtures useful for a wide variety of applications are given below by way of example:

5-amino-4-chloro-2-phenyl-3(2H)-pyridazinone
5-amino-4-bromo-2-phenyl-3(2H)-pyridazinone
5-dimethylamino-4-chloro-2-phenyl-3(2H)-pyridazinone
4,5-dimethoxy-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-dimethylamino-4-chloro-2-m-trifluoromethylphenyl-3(2H)-pyridazinone
5-methylamino-4-chloro-2-m-trifluoromethylphenyl-3(2H)-pyridazinone
4,5-dimethoxy-4-chloro-2-m-trifluoromethylphenyl-3(2H)-pyridazinone
5-methylamino-4-chloro-2-m-α,α,β,β-tetrafluoroethoxyphenyl-3(2H)-pyridazinone
3-(1-methylethyl)-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide
1-methoxymethyl-3-(1-methylethyl)-2,1,3-benzothiadiazin-4(3H)-one-2,2-dioxide
3-(1-methylethyl)-pyrido(2,3-c)-(1,2,8)thiadiazin-4(3H)-one-2,2-dioxide
N-(2-chloroethyl)-2,6-dinitro-N-n-propyl-4-(trifluoromethyl)-aniline
N-n.propyl-2,6-dinitro-N-n-propyl-4-(trifluoromethyl)-aniline
N-(cyclopropylmethyl)-2,6-dinitro-N-n-propyl-4-(trifluoromethyl)-aniline
N-n-butyl-2,6-dinitro-N-ethyl-4-(trifluoromethyl)-aniline
N-n-propyl-2,6-dinitro-N-n-propyl-4-methyl-aniline
N-n-propyl-2,6-dinitro-N-n-propyl-4-aminosulfonyl-aniline
N-n-propyl-2,6-dinitro-N-n-propyl-4-trifluoromethyl-5-amino-aniline
N-pentyl-3-2,6-dinitro-3,4-dimethyl-aniline phenyl-carbamic acid isopropyl ester
(3-chlorophenyl)-carbamic acid-(1-methyl-2-propynyl)-ester
(3-chlorophenyl)-carbamic acid-(4-chlorobutyn-2-yl-1)-ester
(3-chlorophenyl)-carbamic acid isopropyl ester
2-phenyl-carbamoyloxy-N-ethyl-propionamide
O-(n-phenyl-carbamoyl)-propanone oxime
(3-methylphenyl)-carbamic acid-3-[(methoxycarbonyl)-amino]-phenyl ester
phenyl-carbamic acid-3-[(methoxycarbonyl)-amino]-phenyl ester
N-(methyl)-phenyl-carbamic acid-3-[(methoxycarbonyl)-amino]-phenyl ester
bis(1-methylethyl)-thiocarbamic acid-S-(2,3,3-trichloro-2-propenyl)-ester
bis-(1-methylethyl)-thiocarbamic acid-S-(2,3-dichloro-propenyl)-ester
bis(1-methylethyl)-thiocarbamic acid-S-3-ethyl-5-isoxazolylmethyl ester
bis(n-propyl)-thiocarbamic acid ethyl ester
bis(n-propyl)-thiocarbamic acid n-propyl ester
bis(1-methylpropyl)-thiocarbamic acid ethyl ester
bis(2-methylpropyl)-thiocarbamic acid ethyl ester
N-ethyl-N-cyclohexyl-thiocarbamic acid ethyl ester
N-ethyl-N-bicyclo-[2,2,1]-heptyl-thiocarbamic acid ethyl ester
S-(2,3,3-trichloroallyl)-2,2,4-trimethyl-azetidine)-1-carbothiolate
S-(2,3-dichloroallyl)-(2,2,4-trimethyl-azetidine)-1-carbothiolate
2,2-dichloropropionic acid, sodium salt
trichloroacetic acid, sodium salt
2,2-dichlorobutyric acid, sodium salt
benzamido-oxyacetic acid and salts
α-chloro-β-(4-chlorophenyl)-propionic acid methyl ester
N-benzoyl-N-(3,4-dichlorophenyl)-2-amino-propionic acid ethyl ester
N-benzoyl-N-(3-chloro-4-fluorophenyl)-2-amino-propionic acid methyl ester
N-benzoyl-N-(3-chloro-4-fluorophenyl)-2-amino-propionic acid isopropyl ester
2-[4-(2',4'-dichlorophenoxy)-phenoxy]-propionic acid methyl ester
2-[4-(4'-chlorophenoxy)-phenoxy]-propionic acid-2-methylpropyl ester
2-[4-(3,5-dichloropyrydyl-2-oxy)-phenoxy]-propionic acid, sodium salt
2-chloro-4-ethylamino-6-isopropylamino-1,3,5-triazine
chloro-4-ethylamino-6-(2-cyanopropyl-2)-amino-1,3,5-triazine
chloro-4-ethylamino-6-(butyn-1-yl-3)-amino-1,3,5-triazine
chloro-4-ethylamino-6-(1-methyl-2-methoxy-ethyl)-amino-1,3,5-triazine chloro-4-isopropylamino-6-cyclopropylamino-1,3,5-triazine
chloro-4-(1-methyl-2-methoxyethyl)-amino-6-propylamino-1,3,5-triazine
2-chloro-4,6-bis(ethylamino)-1,3,5-triazine
2-chloro-4,6-bis(isopropylamino)-1,3,5-triazine
2-methoxy-4,6-bis(isopropylamino)-1,3,5-triazine
2-thiomethyl-4,6-bis(isopropylamino)-1,3,5-triazine
2-thiomethyl-4-ethylamino-6-isopropylamino-1,3,5-triazine
2-thiomethyl-4-methylamino-6-isopropylamino-1,3,5-triazine
2-thiomethyl-4-ethylamino-6-tert. butylamino-1,3,5-triazine
N,N-dimethyl-2,2-diphenyl-acetamide
N-1-naphthyl-phthalamidic acid
2-(α-naphthoxy)-N,N-diethyl-propionamide
N-(1,1-dimethyl-propynyl)-3,5-dichlorobenzamide
5-acetamido-2,4-dimethyl-trifluoromethanesulfone anilide
N,N-dimethyl-N'-[3-(tert.butylcarbamoyl-oxy)-phenyl]-urea
N-methyl-N'-(2-benzthiazolyl)-urea
N,N-dimethyl-N'-(3,4-dichlorophenyl)-urea
N,N-dimethyl-N'-(3-trifluoromethyl-phenyl)-urea
N,N-dimethyl-N'-(3,5-dichloro-4-methoxy-phenyl)-urea
N-methyl-N-methoxy-N'-(4-chlorophenyl)-urea
N-methyl-N-methoxy-N'-(4-bromophenyl)-urea
N-methyl-N-methoxy-N'-(3-chloro-4-bromophenyl)-urea
N-methyl-N-methoxy-N'-(3,4-dichlorophenyl)-urea
N-methyl-N'-(5-trifluoromethyl-1,3,4-thiadiazolyl-2)-urea imidazolidin-2-one-1-carboxylic acid isobutylamide
2,4'-dinitro-4-trifluoromethyl-diphenyl ether
2-chloro-4-trifluoromethyl-3'-ethoxy-4'-nitro-diphenyl ether
2-chloro-4-trifluoromethyl-3'-carboxy-4'-nitro-diphenyl ether and salts
2,4-dichloro-3'-methoxycarbonyl-4'-nitro-diphenyl ether
3-methylthio-4-amino-6-tert.butyl-1,2,4-triazin-5(4H)-one
3-methyl-4-amino-6-phenyl-1,2,4-triazin-5(4H)-one
3-(1-methylethyl)-5-bromo-6-methyl-uracil
3-(tert.butyl)-5-chloro-6-methyl-uracil
3-(tetrahydropyranyl-2)-5-chloro-6-methyl-uracil
3-cyclohexyl-5,6-trimethylene-uracil
2-ethoxy-2,3-dihydro-3,3-dimethyl-5-benzofuranyl-methylsulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-methyl-acetylaminosulfonate
2-(3,4-dichlorophenyl)-4-methyl-1,2,4-oxadiazolidine-3,5-dione
3-[1-(N-ethoxyamino)-propylidene]-6-ethyl-3,4-dihydro-2-H-pyran-2,4-dione
2-[1-(N-allyloxyamino)-propylidene]-5,5-dimethylcyclohexane-1,3-dione
sodium salt of 2-[1-(N-allyloxyamino)-butylidene]-5,5-dimethyl-4-methoxy-carbonyl-cyclohexane-1,3-dione
2-[1-(N-allyloxyamino)-butylidene]-5,5-dimethyl-4-methoxycarbonyl-cyclohexane-1,3-dione
3,5,6-trichloro-4-amino-picolinic acid and salts and esters
1,1'-dimethyl-4,4'-dipyridylium-di(methylsulfate)
1,1'-ethylene-2,2'-dipyridylium dibromide
dimethyl-2,3,5,6-tetrachloroterephthalate
2,6-dichlorobenzonitrile
3-amino-2,5-dichlorobenzoic acid and salts and esters
2-methoxy-3,6-dichlorobenzoic acid and salts and esters
2,4-dichlorophenoxyacetic acid and salts and esters
3-amino-1,2,4-triazole
3-phenylsulfonyl-2-methyl-trifluoromethanesulfone-anilide
N-(phosphonomethyl)-glycine and salts
2,3-dihydro-5,6-dimethyl-1,4-dithiin-1,1,4,4-tetroxide
2-(1-methylpropyl)-4,6-dinitro-phenol and salts and esters
1-allyloxy-1-(4-bromophenyl)-2-[1',2',4'-triazolyl-(1')]-ethane and salts
(4-bromophenyl)-3.4.5.9.10-pentaazatetracyclo-[5.4.1.0$^{2.6}$.0.$^{8.11}$]-dodeca-3.9-diene
1,3-dimethyl-4-(2,4-dichlorobenzoyl)-5-pyrazolyl-4-toluene sulfonate
1-methyl-3-phenyl-5-[3-(trifluoromethyl)-phenyl]-4-(1H)-pyridinone
N-(α,α-dimethylbenzyl)-N'-(4-methylphenyl)-urea
[1-(1',2',4'-triazolyl-1')-1-(4'-chlorophenoxy)]-3,3-dimethyl-butan-2-one
2-chloro-N,N-diallyl-acetamide
2-chloro-N-isopropyl-acetanilide
2-chloro-N-butyn-(1)-yl-(3)-acetanilide
2-chloro-N-methoxymethyl-2,6-diethyl-acetanilide
2-chloro-N-ethoxymethyl-2-methyl-6-ethyl-acetanilide
2-chloro-N-n-butoxymethyl-2,6-diethyl-acetanilide
2-chloro-N-isobutoxymethyl-2,6-dimethyl-acetanilide
2-chloro-N-methoxyethyl-2,6-dimethyl-acetanilide
2-chloro-N-methoxy-1-methylethyl-2-methyl-6-ethyl-acetanilide
2-chloro-N-ethoxycarbonylmethyl-2,6-diethyl-acetanilide
2-chloro-N-isopropoxycarbonylmethyl-2-methyl-6-ethyl-acetanilide
2-chloro-N-(1,3-dioxolan-2-yl)-methyl-2,6-dimethyl-acetanilide
2-chloro-N-isopropyl-2,3-dimethyl-acetanilide
2-chloro-N-(pyrazol-1-yl-methyl)-2,6-dimethyl-acetanilide
2-chloro-N-(pyrazol-1-yl-methyl)-2-methyl-6-ethyl-acetanilide
2-chloro-N-(4-methylpyrazol-1-yl-methyl)-2,6-dimethyl-acetanilide
2-chloro-N-(4-methylpyrazol-1-yl)-methyl)-2,3,6-trimethyl-acetanilide
2-chloro-N-(4-methoxypyrazol-1-yl-methyl)-2-methyl-6-ethyl-acetanilide
2-chloro-N-(1,2,4-triazol-1-yl-méthyl)-2,6-dimethyl-acetanilide.

It may also be useful to apply the new compounds, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Oils of various types, wetting agents, spreader-stickers and antifoams may also be added to the individual active ingredients or mixtures thereof.

TABLE 1

| List of test plants | |
| --- | --- |
| Botanical name | Common name |
| *Abutilon theophrasti* | velvet leaf |

TABLE 1-continued
List of test plants

| Botanical name | Common name |
| --- | --- |
| Amaranthus retroflexus | redroot pigweed |
| Arachis hypogaea | peanuts (groundnuts) |
| Avena sativa | oats |
| Beta vulgaris | sugarbeets |
| Centaurea cyanus | cornflower |
| Chrysanthemum segetum | corn marigold |
| Cyperus esculentus | yellow nutsedge |
| Echinochloa crus galli | barnyardgrass |
| Euphorbia geniculata | South American member of spurge family |
| Galium aparine | catchweed bedstraw |
| Gossypium hirsutum | cotton |
| Ipomoea spp. | morningglory |
| Lolium multiflorum | annula ryegrass |
| Matricaria spp. | chamomile |
| Mentha piperita | peppermint |
| Nicandra physalodes | apple of Peru |
| Sesbania exaltata | hemp sesbania (coffeeweed) |
| Sinapis alba | white mustard |
| Solanum nigrum | black nightshade |
| Sorghum bicolor | sorghum |
| Stellaria media | chickweed |
| Triticum aestivum | wheat |
| Veronica perisca | birdseye speedwell |

TABLE 2
Herbicidal action of parabanic acids on pre- and postemergence application in the greenhouse

| | Compound no. 1 Damage (%) at 3.0 kg/ha | |
| --- | --- | --- |
| Test plant | Preemergence | Postemergence |
| Avena sativa | 80 | 100 |
| Centaurea cyanus | — | 100 |
| Cyperus esculentus | — | 100 |
| Echinochloa crus galli | 90 | 100 |
| Galium aparine | — | 100 |
| Ipomoea spp. | 100 | 100 |
| Lolium multiflorum | 100 | 100 |
| Mentha piperita | — | 100 |
| Sinapis alba | 100 | — |

0 = no damage
100 = nonemergence, or plants withered

TABLE 3
Selective herbicidal action of parabanic acid derivatives; preemergence application in the greenhouse

| Test plant | Compound no. 4 Damage (%) at 0.5 kg/ha |
| --- | --- |
| Sorghum bicolor | 0 |
| Abutilon theophrasti | 98 |
| Amaranthus retroflexus | 98 |
| Chrysanthemum segetum | 100 |
| Centaurea cyanus | 98 |
| Euphorbia geniculata | 100 |
| Matricaria spp. | 95 |
| Nicandra physalodes | 100 |
| Sesbania exaltata | 98 |
| Stellaria media | 98 |

0 = no damage
100 = nonemergence, or plants withered

TABLE 4
Selective herbicidal action of parabanic acid derivatives; pre- and postemergence application in the greenhouse

| | Compound no. 55 % damage at 1.0 kg/ha | |
| --- | --- | --- |
| Test plant | Preemergence | Postemergence |
| Arachys hypogaea | 0 | 0 |
| Gossypium hirsutum | 0 | — |
| Sorghum bicolor | 0 | 10 |

TABLE 4-continued
Selective herbicidal action of parabanic acid derivatives; pre- and postemergence application in the greenhouse

| | Compound no. 55 % damage at 1.0 kg/ha | |
| --- | --- | --- |
| Test plant | Preemergence | Postemergence |
| Triticum aestivum | 0 | 0 |
| Amaranthus retroflexus | 80 | 100 |
| Ipomoea spp. | 98 | 80 |
| Sesbania exaltata | 100 | 100 |
| Solanum nigrum | 98 | — |
| Stellaria media | — | 100 |
| Veronica persica | 90 | — |

0 = no damage
100 = nonemergence or plants withered

TABLE 5
Herbicidal action of parabanic acid derivatives with selectivity in different crops; preemergence application in the greenhouse

| Test plant | Compound no. 21 % damage at 2.0 kg/ha |
| --- | --- |
| Arachys hypogaea | 0 |
| Beta vulgaris | 0 |
| Gossypium hirsutum | 0 |
| Sorghum bicolor | 0 |
| Amaranthus retroflexus | 100 |
| Chrysanthemum segetum | 90 |
| Sesbania exaltata | 90 |
| Solanum nigrum | 98 |
| Veronica persica | 90 |

0 = no damage
100 = nonemergence or plants withered

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possble.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

There may be added to the mixtures or individual active ingredients oils of various types, herbicides, fungicides, nematocides, insecticides, bactericides, trace elements, fertilizers, antifoams (e.g., silicones), growth regulators, antidotes and other effective compounds.

EXAMPLE 2

90 Parts by weight of compound 1 is mixed with 10 parts by weight of N-methyl-α-pyrrolidone. A mixture is obtained which is suitable for application in the form of very fine drops.

EXAMPLE 3

20 Parts by weight of compound 3 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 4

20 Parts by weight of compound 1 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 5

20 Parts by weight of compound 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 6

20 Parts by weight of compound 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 7

3 Parts by weight of compound 1 is intimately mixed with 97 parts by weight of particulate kaolin. A dust is obtained containing 3% by weight of the active ingredient.

EXAMPLE 8

30 Parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 9

40 Parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 10

20 Parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A parabanic acid derivative of the formula

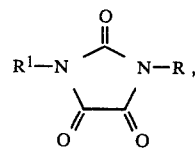

where $R^1$ denotes alkyl of 1 to 4 carbon atoms, 2-chloroethyl, 2-methoxyethyl, methoxymethyl, allyl, 2-chloropropen-(1)-yl-(3), buten-(1)-yl-(3), propargyl, butyn-(1)-yl-(3), 1-chlorobutyn-(2)-yl-(4), cyclopentyl, cyclohexyl, 3-methylcyclohexyl, 2,6-dimethylcyclohexyl or cyclopropyl and R denotes phenoxyphenyl which is unsubstituted or is substituted in one or both rings by alkyl of 1 to 3 carbon atoms, alkyl of 1 to 3 carbon atoms substituted by 1 to 3 halo atoms, methoxymethyl, cyclohexyl, benzyl, methoxy, ethoxy, methoxy or ethoxy substituted by 1 to 2 halo atoms, from 1 to 3 halo atoms, methylthio, phenyl, thiocyanato, cyano

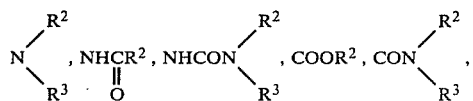

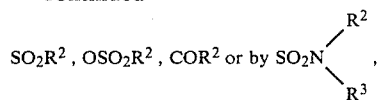

$R^2$ and $R^3$ being identical or different and each denoting hydrogen or having the meanings given for $R^1$.

2. A parabanic acid derivative as set forth in claim 1, wherein $R^1$ is methyl.

3. A parabanic acid derivative selected from the group consisting of 1-(3'-fluoro-4'-(phenoxy)-phenyl)-3-methylparabanic acid, and 1-(3'-chloro-4'-(phenoxy)-phenyl)-3-methylparabanic acid.

* * * * *